US006878541B2

(12) United States Patent
Qiao et al.

(10) Patent No.: US 6,878,541 B2
(45) Date of Patent: Apr. 12, 2005

(54) PAPILLOMA PSEUDO-VIRUS AND PREPARATION

(76) Inventors: Liang Qiao, Stritch School of Medicine, 2160 S. First Ave., Maywood, IL (US) 60153; Wei Shi, Stritch School of Medicine, 2160 S. First Ave., Maywood, IL (US) 60153; Yujun Huang, Stritch School of Medicine, First Ave., Maywood, IL (US) 60153; Jianzhong Liu, Stritch School of Medicine, 2160 S. First Ave., Maywood, IL (US) 60153

( * ) Notice: Subject to any disclaimer, the term of this patent is extended or adjusted under 35 U.S.C. 154(b) by 0 days.

(21) Appl. No.: 10/294,087

(22) Filed: Nov. 14, 2002

(65) Prior Publication Data

US 2003/0129728 A1 Jul. 10, 2003

Related U.S. Application Data

(63) Continuation of application No. PCT/CN02/00187, filed on Mar. 22, 2002.

(30) Foreign Application Priority Data

May 15, 2001 (CN) ........................................ 01118003 A

(51) Int. Cl.[7] .............................................. C12N 15/00
(52) U.S. Cl. ............................... 435/320.1; 435/235.1; 435/239
(58) Field of Search .......................... 424/199.1, 204.1; 435/320.1, 235.1, 239

(56) References Cited

U.S. PATENT DOCUMENTS 6,420,160 B1 * 7/2002 Bloch ......................... 435/239

FOREIGN PATENT DOCUMENTS

| WO | WO 98/02548 | * | 1/1998 |
| WO | WO 99/13056 | * | 3/1999 |

OTHER PUBLICATIONS

Touze et al, Nucleic Acid Reasearch, 1998, vol. 26, No. 5, pp. 1317–1323.*
Fayad et al, Journal of Immunology, 2004, vol. 173, pp. 2692–2698.*

Zhang et al, Journal of Virology, 2004, vol. 78, No. 19, pp. 10249–10257.*

Touze, et al "In Vitro Gene Transfer Using Human Papillomavirus–like Particles," Nucleic Acids Research, 1998, vol. 26, No. 5, pp. 1317–1323.

Kawana, et al "In Vitro Construction of Pseudovirions of Human Papillomavirus Type 16: Incorporation of Plasmid DNA Into Reassembled L1/L2 Capsids," Journal of Virology, Dec. 1998, vol. 72, No. 12, pp. 10298–10300.

Shi, et al Induction of Mucosal CTL Responses by Papillomavirus Pseudovirions, American Association of Immunologists and Clinical Immunology Society Joint Annual Meeting, Immunology 2000, May 12–16, 2000, Abstracts 34.1–200.30, No. 48.14.

Shi, et al "Papillomavirus Pseudovirions as a Novel Mucosal Vaccine," HPV 2000 Barcelona, Immunology/HIV/Vaccines: Poster Session 3, Abstract No. 448.

Shi, et al "Papillomavirus Pseudovirions Induce a Stronger CTL Response Than a DNA Vaccine," HPV 2000 Barcelona, Immunology/HIV/Vaccines: Poster Session 3, Abstract No. 454.

Shi, et al "Papillomavirus Pseudovirus: a Novel Vaccine To Induce Mucosal and Systemic Cytotoxic T–Lymphocyte Responses," Journal of Virology, Nov. 2001, vol. 75, No. 21, pp. 10139–10148.

* cited by examiner

Primary Examiner—Ali R. Salimi
(74) Attorney, Agent, or Firm—Henneman & Saunders; Larry E. Henneman, Jr.

(57) ABSTRACT

The invention involves a papilloma pseudo-virus that can induce immune response after oral intake as well as its preparation. It is characterized in that HPV or BPV pseudo-virus are made by disrupting HPV-VLP or BPV-VLP, mixing them with plasmids (plasmids or DNA vaccine), and reassembling them into the pseudo-viruses (VLPs with plasmids inside). Oral administration of the pseudo-viruses will result in delivery to mucosal and systemic lymphoid tissues and induce immune responses for disease prevention and treatment. The pseudo-virus induces stronger immune response than DNA vaccines. Additionally, the pseudo-virus can be applied in gene therapy by bringing the therapeutic genes into lymphoid tissues in the human body.

18 Claims, No Drawings

PAPILLOMA PSEUDO-VIRUS AND PREPARATION

RELATED APPLICATIONS

This application claims the right of priority under 35 U.S.C. §120, as authorized by 35 U.S.C. §365(c), to International Application No. PCT/CN02/00187 filed on Mar. 22, 2002 by the same inventors, which claims priority to Application No. 01118003.X filed in China on May 15, 2001 (not published in English), both of which are incorporated herein by reference in their entirety.

TECHNICAL FIELD

The subject of the invention is a new vector for oral immunization by using a papillomavirus pseudovirus. This pseudovirus can be used as a vaccine to treat and prevent mucosal infections by pathogens or mucosal tumors. Additionally it can be used in gene therapy.

TECHNICAL BACKGROUND

It is well known that pathogens and immune deficiency are the major causes of various diseases. The human body is frequently invaded by pathogens and damaged by tumors. Therefore, immunity is necessary in protecting the human body from various infections and damages. Many vaccines currently used induce specific immune responses through subcutaneous and intramuscular injections and help the body survive the disease. However, the injections can only induce systemic immune responses but not mucosal immune responses. The injected vaccine fails to treat and prevent those pathogens transmitted through mucosa. Actually many diseases are transmitted through mucosa, for example, HIV.

SUMMARY OF THE INVENTION

The objective of this invention is to make a papillomavirus pseudovirus that is similar to a papillomavirus, but without the capacity of causing disease, and to insert genes or DNA vaccines into papillomavirus-like particles (VLPs) so that it can be used for oral delivery of these genes to mucosal and systemic lymphoid tissues to induce immune responses for disease prevention and treatment.

The pseudo-virus described above is made by disrupting human papilloma virus (HPV)-VLP or bovine papilloma virus (BPV)-VLP, mixing them with plasmids, and reassembling the VLPs with the plasmids inside the VLPs to form the pseudovirus. Thus, the pseudovirus has viral VLPs but may not have any papillomavirus DNA. After the DNA vaccine has been packaged into VLPs, the vaccine can be delivered orally to the mucosal and systemic immune systems. The vaccine in the present application does not contain DNA of the papilloma virus. The DNA vaccine will induce only systemic immune responses by subcutaneous or intramuscular injections. In other words, the pseudo-virus in the invention is the papillomavirus VLPs that contain the DNA vaccine. It is prepared by the following steps:

1. HPV-VLPs or BPV-VLPs are mixed with a disruption buffer in 1:1 ratio by vol., and incubated 60 minutes at room temperature; the disruption buffer: ethylene glycol bis(2-aminoethylether) tetraacetic acid (EGTA) 20 mM, dithiothreitol (DTT) 40 mM, sodium chloride (NaCl) 300 mM, Tris-hydrochloric acid (Tris-HCl)(pH 8.0) 100 mM;

2. Plasmids are added in 1/10 of vol, 0.5–1.0 microgram/microliter;

3. A stop buffer is added progressively. The stop buffer; calcium chloride ($CaCl_2$) 25 mM, dimethyl sulfoxide (DMSO) 20% (total stop buffer in vol.); and 4. The mixture is incubated at 4 centigrade for 4 to 12 hours.

DETAILED DESCRIPTION OF PARTICULAR EMBODIMEMT

This pseudo-virus does not cause any disease, and thus can be used for gene therapy. The gene of interest can be inserted into a plasmid that is then packaged into VLPs. Oral administration of the pseudovirus will deliver the gene to intestinal mucosal and systemic lymphoid tissues as well as mucosal epithelium. More importantly, an antigen can be inserted into a plasmid which is packaged into the VLPs to form pseudoviruses, which serve as an oral vaccine to induce protective immune responses. This is different from other vaccines because most other vaccines can only be injected subcutaneously or intramuscularly, but can not be given orally. Other vaccines can induce only systemic immune responses, but not mucosal immune responses. Because many pathogens are transmitted through mucosa, only this pseudovirus can induce effective immune responses to prevent and to treat mucosal infections caused by pathogens. These pathogens include bacteria such as *salmonella* and viruses such as HIV. Similarly, this pseudo-virus can be used to induce immune responses to treat tumors, in particular, mucosal tumors such as colon cancer. This pseudo-virus also induces much stronger immune responses than DNA vaccines.

EXAMPLE 1

First, HPV-VLPs were mixed with disruption buffer at 1:1 proportion by vol., and then incubated at room temperature for 60 min. The disruption buffer was composed of ethylene glycol bis(2-aminoethylether) tetraacetic acid (EGTA) 20 mM, dithiothreitol (DTT) 40 mM, sodium chloride (NaCl) 300 mM, and Tris-hydrochloric acid (Tris-HCl)(pH 8.0) 100 mM. Then, the plasmids (PCI-GLP-LCMV) were added into the mixture in 0.5 microgram/microliter by ratio of 1/10 in vol. Next, stop buffer was progressively added, and the mixture was incubated at 4 centigrade overnight. The stop buffer was composed of calcium chloride ($CaCl_2$) 25 mM and dimethyl sulfoxide (DMSO) 20% (in vol.). The pseudovirus was subcutaneously injected into C57BL6 mice. Meanwhile, the unpackaged plasmids were injected directly into mice as a control. It was found that the pseudo-virus induced more CTLs than the unpackaged plasmids did by using Cr51 release assay or gamma interferon Elispot. The conclusion is that the pseudo-virus is more effective than DNA vaccines in inducing cellular immune response.

EXAMPLE 2

First, BPV-VLPs were mixed with disruption buffer at 1:1 proportion by vol., and then incubated at room temperature for 60 min. The disruption buffer was composed of EGTA 20 mM, DTT 40 mM, NaCl 300 mM, and Tris-hydrochloric acid (Tris-HCl) (pH 8.0) 100 mM. Then, plasmids expressing GLP (Green lantern protein) were added into the mixture in 0.5 microgram/microliter by ratio of 1/10 in vol. Next, the same volume of stop buffer was gradually added, and the mixture was incubated at 4 centigrade overnight. The stop buffer was composed of $CaCl_2$ 25 mM, and DMSO 20% (in vol.). The pseudoviruses were orally administered into mice, and the expression of GLP was examined. GLP was found in intestinal mucosa, mesenteric lymph nodes, and spleen. It is thus demonstrated that the pseudovirus can carry genes to intestinal mucosa and the entire immune system. Therefore, it can be used in gene therapy.

When mice were orally administered with unpackaged plasmids encoding GLP, GLP was not found in these tissues.

EXAMPLE 3

By the same method as described in example 1, a pseudo-virus expressing HPV16E7 (HPV and BPV pseudo-viruses) was prepared and given to mice orally. The pseudovirus induced specific mucosal and systemic CTLs to the E7 antigen. However, oral immunization with unpackaged plasmid encoding the E7 could not induce any immune response. Therefore, the pseudovirus can be used to induce mucosal and systemic immune responses.

EXAMPLE 4

By the same method as described in examples 1 and 2, pseudo-viruses expressing HPV16E7 (HPV and BPV pseudo-viruses) were made by using HPV and BPV VLPs respectively. Mice were orally administered with HPV pseudo-virus encoding E7 and then challenged with BPV pseudo-virus encoding E7. It was found that HPV pseudo-virus prevented mice from the challenge with BPV pseudo-virus. Therefore, HPV pseudo-virus can provide protective immunity.

EXAMPLE 5

By the same method as described in examples 1 and 2, the pseudovirus expressing human interleukin 2 (IL-2) was made. Via oral administration, the pseudovirus expressing IL-2 entered intestinal mucosal and systemic lymphoid tissues. It was found that it enhanced the efficacy of generation of mucosal immunity.

What is claimed is:

1. A method for treating a patient with a papillomavirus pseudo-virus including plasmids, said method comprising:
    making a papillomavirus pseudo-virus by
        disrupting papillomavirus-VLPs by mixing said papillomavirus-VLPs with a disruption buffer, said disruption buffer including EGTA 20mM, DTT 40 mM, NaCl 300mM, and Tris-hydrochloric acid (Tris-HCl) (pH 8.0) 100mM,
        incubating the mixture for 60 minutes at room temperature,
        mixing said disrupted papillomavirus-VLPs with said plasmids by adding said plasmids to the mixture in 1/10 ratio, said plasmids being at a concentration 0.5–1.0 microgram/microliter,
        adding a stop buffer gradually to reassemble said papillomavirus-VLPs and said plasmids into pseudo-viruses of VLPs with said plasmids inside, said stop buffer including CaCl, 25mM and DMSO 20% by volume, and
        incubating the mixture at 4 centigrade from 4 to 12 hours; and
    administering said pseudo-virus via the mucosa of said patient to induce a mucosal response.

2. A method according to claim 1, wherein said plasmids include a gene of a pathogen.

3. A method according to claim 1, wherein said plasmids include therapeutic genes.

4. A method according to claim 1, wherein said papillomavirus-VLPs are mixed with said disruption buffer in a 1:1 ratio by volume.

5. A method according to claim 1, wherein;
    the total volume of stop buffer equals the combined total volume of said papillomavirus-VLPs, said disruption buffer, and said plasmids.

6. A method according to claim 1, wherein said papillomavirus-VLPs are human papillomavirus-VLPs.

7. A method according to claim 1, wherein said papillomavirus-VLPs arc bovine papillomavirus-VLPs.

8. A method according to claim 1, wherein said pseudo-virus is administered to said patient orally.

9. A method according to claim 8, wherein said pseudo-virus is administered to said patient to induce a mucosal immune response in said patient.

10. A method according to claim 9, wherein said mixture pseudo-virus is administered to said patient to further induce a systemic immune response.

11. A method according to claim 1, wherein said pseudo-virus is administered to said patient to induce a mucosal immune response in said patient.

12. A method according to claim 11, wherein said pseudo-virus is administered to said patient to further induce a systemic immune response.

13. A method according to claim 3, wherein said pseudo-virus is administered said patient to deliver said therapeutic genes to the cells of said patient.

14. A method according to claim 13, wherein said pseudo-virus is administered to said patient orally.

15. A method according to claim 14, wherein said therapeutic genes are delivered to the mucosa of said patient.

16. A method according to claim 15, wherein said therapeutic genes are delivered to the systemic immune system of said patient.

17. A method according to claim 13, wherein said therapeutic genes are delivered to the mucosa of said patient.

18. A method according to claim 1, wherein said plasmids express interleukin 2.

* * * * *

UNITED STATES PATENT AND TRADEMARK OFFICE
CERTIFICATE OF CORRECTION

PATENT NO.   : 6,878,541 B2
DATED        : April 12, 2005
INVENTOR(S)  : Qiao et al.

It is certified that error appears in the above-identified patent and that said Letters Patent is hereby corrected as shown below:

Column 3,
Line 50, delete "CaCl" and insert -- $CaCl_2$ -- between "including" and "25mM";

Column 4,
Line 21, delete "arc" and insert -- are -- between "papillomavirus-VLPs" and "bovine"; and
Line 27, delete "mixture", from between "said" and "pseudo-virus".

Signed and Sealed this

Nineteenth Day of July, 2005

JON W. DUDAS
*Director of the United States Patent and Trademark Office*